US010036689B2

(12) United States Patent
Shibata et al.

(10) Patent No.: US 10,036,689 B2
(45) Date of Patent: Jul. 31, 2018

(54) BIOLOGICAL TISSUE CUTTING DEVICE AND USE THEREOF

(71) Applicant: JMS CO., LTD., Hiroshima-shi, Hiroshima (JP)

(72) Inventors: Kazuhiro Shibata, Kyoto (JP); Noritaka Isogai, Osaka (JP); Koji Suzuki, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 0 days.

(21) Appl. No.: 15/115,491

(22) PCT Filed: Jan. 27, 2015

(86) PCT No.: PCT/JP2015/052225
§ 371 (c)(1),
(2) Date: Jul. 29, 2016

(87) PCT Pub. No.: WO2015/115439
PCT Pub. Date: Aug. 6, 2015

(65) Prior Publication Data
US 2017/0191906 A1      Jul. 6, 2017

(30) Foreign Application Priority Data

Jan. 29, 2014 (JP) ................................. 2014-014859

(51) Int. Cl.
*G01N 1/04* (2006.01)
*G01N 1/28* (2006.01)
(Continued)

(52) U.S. Cl.
CPC ............ *G01N 1/286* (2013.01); *A61B 17/32* (2013.01); *A61B 17/3209* (2013.01); *G01N 1/04* (2013.01);
(Continued)

(58) Field of Classification Search
CPC .................................. G01N 1/04; G01N 1/28
(Continued)

(56) References Cited

U.S. PATENT DOCUMENTS 5,396,898 A * 3/1995 Bittmann ............ B02C 19/0056
241/277
5,752,425 A   5/1998 Asakura et al.
(Continued)

FOREIGN PATENT DOCUMENTS

CN        102636370        8/2012
JP        4-077848         7/1992
(Continued)

OTHER PUBLICATIONS

Extended European Search Report issued in corresponding European Patent Application No. 15742545.5, dated Aug. 7, 2017, 7 pages.
(Continued)

*Primary Examiner* — Arlen Soderquist
(74) *Attorney, Agent, or Firm* — Hamre, Schumann, Mueller & Larson, P.C.

(57) ABSTRACT

The present invention provides a biological tissue cutting device that can produce minute fragments of a biological tissue easily and efficiently. The biological tissue cutting device for producing tissue fragments by cutting a biological tissue includes: a first cutting unit configured to form a cut surface extending in a first direction by cutting the biological tissue on a stage; and a second cutting unit configured to form a cut surface extending in a second direction and a cut surface extending in a third direction by cutting the biological tissue on the stage. The planar direction of the cut surface extending in the second direction is a direction crossing the cut surface extending in the first direction, and the planar direction of the cut surface extending in the third direction
(Continued)

is a direction crossing the cut surface extending in the first direction and the cut surface extending in the second direction.

14 Claims, 6 Drawing Sheets

(51) Int. Cl.
  *G01N 1/30*    (2006.01)
  *A61B 17/32*    (2006.01)
  *A61B 17/3209*   (2006.01)

(52) U.S. Cl.
  CPC ....... *G01N 1/30* (2013.01); *G01N 2001/2873* (2013.01)

(58) Field of Classification Search
  USPC ................... 436/174; 606/131–132, 167
  See application file for complete search history.

(56) References Cited

U.S. PATENT DOCUMENTS

| | | | | |
|---|---|---|---|---|
| 5,784,937 A * | 7/1998 | Wygal | ...................... | B26D 3/22 |
| | | | | 198/592 |
| 6,248,114 B1 * | 6/2001 | Ysebaert | .............. | A61B 17/322 |
| | | | | 606/132 |
| 6,387,653 B1 * | 5/2002 | Voneiff | .................... | G01N 1/06 |
| | | | | 435/40.5 |
| 6,549,823 B1 * | 4/2003 | Hicks | ........................ | B26D 3/18 |
| | | | | 700/159 |
| 7,374,907 B1 * | 5/2008 | Voneiff | .................... | G01N 1/06 |
| | | | | 156/64 |
| 7,540,221 B1 * | 6/2009 | Schmidt | .................... | B26D 3/18 |
| | | | | 83/35 |
| 7,600,457 B2 * | 10/2009 | Voneiff | .................... | G01N 1/06 |
| | | | | 83/307.1 |
| 7,651,507 B2 * | 1/2010 | Mishra | ................. | A61B 17/322 |
| | | | | 606/131 |
| 7,926,401 B2 * | 4/2011 | Mishra | ................. | A61B 17/322 |
| | | | | 407/30 |
| 7,955,336 B2 * | 6/2011 | Gil | ........................ | A61F 2/4644 |
| | | | | 606/79 |
| 8,065,945 B2 * | 11/2011 | Kobayashi | ............. | A61B 10/02 |
| | | | | 30/173 |
| 8,497,121 B2 * | 7/2013 | Yao | ........................ | A61K 35/32 |
| | | | | 424/426 |
| 8,535,239 B2 * | 9/2013 | Conlon | .............. | A61B 10/0275 |
| | | | | 600/562 |
| 2004/0176787 A1 * | 9/2004 | Mishra | ................. | A61B 17/322 |
| | | | | 606/167 |
| 2004/0243112 A1 | 12/2004 | Bendett et al. | | |
| 2005/0072285 A1 | 4/2005 | Lang et al. | | |
| 2005/0152760 A1 | 7/2005 | Ranner | | |
| 2006/0106378 A1 * | 5/2006 | Kobayashi | ............. | A61B 10/02 |
| | | | | 606/45 |
| 2007/0179516 A1 * | 8/2007 | Mishra | ................. | A61B 17/322 |
| | | | | 606/167 |
| 2008/0255562 A1 * | 10/2008 | Gil | ........................ | A61F 2/4644 |
| | | | | 606/79 |
| 2009/0223387 A1 * | 9/2009 | Schmidt | .................. | B26D 3/18 |
| | | | | 99/537 |
| 2009/0293689 A1 | 12/2009 | Ichihara | | |
| 2010/0082044 A1 * | 4/2010 | Mishra | ................. | A61B 17/322 |
| | | | | 606/132 |
| 2011/0059415 A1 | 3/2011 | Kasenbacher | | |
| 2011/0282239 A1 * | 11/2011 | Conlon | .............. | A61B 10/0275 |
| | | | | 600/566 |
| 2014/0255978 A1 | 9/2014 | Morimoto | | |

FOREIGN PATENT DOCUMENTS

| | | |
|---|---|---|
| JP | 2007-527731 | 10/2007 |
| JP | 2009-288169 | 12/2009 |
| JP | 2011-512914 | 4/2011 |
| WO | 01/27586 | 4/2001 |
| WO | 2013/077337 | 5/2013 |

OTHER PUBLICATIONS

Action for the corresponding Japanese Patent Application No. 2015-559952 dated Jun. 14, 2017, 8 pages with a partial translation.

* cited by examiner

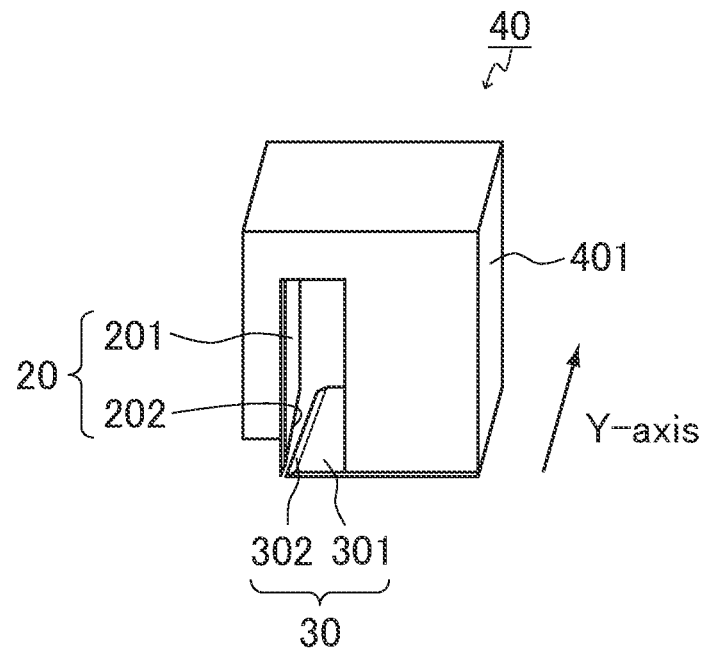
FIG. 3A
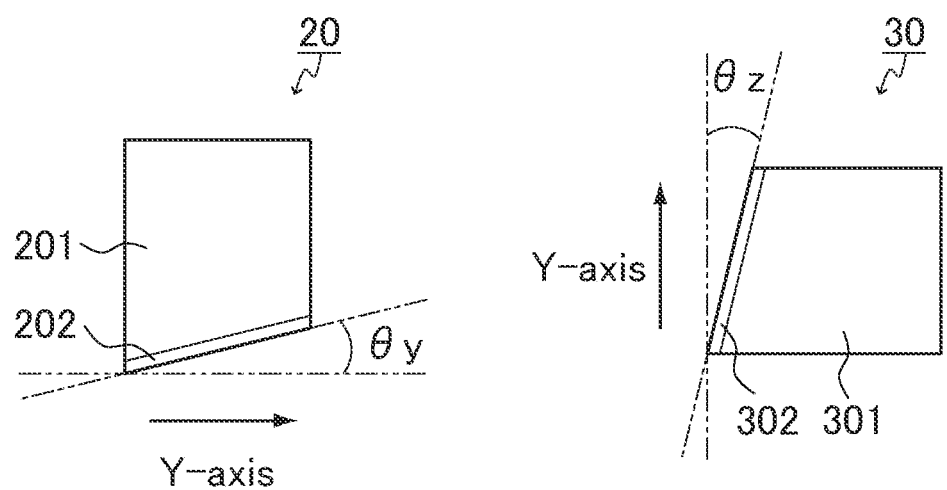
FIG. 3B
FIG. 3C

BIOLOGICAL TISSUE CUTTING DEVICE AND USE THEREOF

TECHNICAL FIELD

The present invention relates to a biological tissue cutting device for producing tissue fragments by cutting a biological tissue and use thereof.

BACKGROUND ART

In the field of medical treatment, regenerative medicine is attracting particularly high attention and being studied extensively. A method generally employed in the regenerative medicine is to collect cells from an autologous or allogeneic tissue, seed the collected cells to a regeneration scaffold to culture the cells, and use the thus-obtained cultured cells.

However, in this method, the adhesion of the collected cells to the regeneration scaffold is important. Accordingly, it is important to set appropriate culture conditions etc., which may take time and effort.

CITATION LIST

Patent Document(s)

Patent Document 1: JP 2011-512914 A
Patent Document 2: JP 2007-527731 A

BRIEF SUMMARY OF THE INVENTION

Problem to be Solved by the Invention

In recent years, a novel method in regenerative medicine not involving culture has been proposed. Specifically, in this method, stem cells or mature cells are grafted into the site of injury or defect in a biological tissue, and the tissue is repaired and regenerated utilizing the proliferation and differentiation potency of the grafted cells. However, the grafted cells exhibit a low survival rate in vivo and thus achieve low functional expression efficiency. Thus, according to this method, a desired repairing and regenerating effect may not be obtained. On this account, as a method for solving this problem, grafting a tissue, which is a functional aggregate of cells, is now under study. In the case of cartilage, for example, a minute tissue fragment cut out from the cartilage is grafted into a living body, instead of culturing chondrocytes collected from the cartilage. In this case, in a place of surgical operation, cartilage can be taken out from a patient, and a tissue fragment can be cut out from the cartilage and grafted into the living body of the patient. Thus, it is possible to realize regenerative medicine of operating room completion type. This method eliminates the necessity of not only the culture after the surgical operation but also reoperation after the culture. Therefore, this method enables regenerative therapy with smaller burden on patients and doctors at low cost.

However, in the case of a large tissue fragment, nutrients cannot be supplied sufficiently to the inside of the grafted tissue fragment, resulting in insufficient engraftment of the tissue fragment in vivo. On this account, there is a demand for production of a large number of minute tissue fragments with uniform size so as to enable supply of nutrients into the inside of the tissue fragments when they are grafted. Furthermore, in the field of regenerative medicine, in order to promote regeneration efficiently and safely, it is important to obtain, as regeneration sources, as many tissue fragments as possible from a limited amount of a biological tissue. To this end, there is a demand for a technique for cutting a biological tissue finely to provide a large number of tissue fragments.

On the other hand, as a device for cutting a biological tissue, a device utilizing a laser beam has been reported, for example (see Patent Documents 1 and 2, for example). However, biological tissues for use in regenerative medicine as described above are very soft and fragile. Besides, they are wet with being filled with a body fluid or a culture solution. Thus, with the above-described device, it is difficult to cut a biological tissue into minute tissue fragments for use in regenerative medicine. Also, no cutting device specialized for the production of the above-described tissue fragments for use in regenerative medicine has not yet been reported. Thus, in the field of regenerative medicine, skilled persons manually cut a biological tissue into tissue fragments. This operation cannot be performed by unskilled persons, and even skilled persons can perform this operation with poor operation efficiency. Accordingly, it is difficult to obtain a large number of tissue fragments in a short time.

With the foregoing in mind, it is an object of the present invention to provide a biological tissue cutting device that can produce minute tissue fragments from a biological tissue easily and efficiently.

Means for Solving Problem

The present invention provides a biological tissue cutting device for producing a tissue fragment by cutting a biological tissue, including: a stage unit including a stage on which a biological tissue is fixed; a first cutting unit configured to form a cut surface extending in a first direction by cutting the biological tissue on the stage; and a second cutting unit configured to form a cut surface extending in a second direction and a cut surface extending in a third direction by cutting the biological tissue on the stage, wherein a planar direction of the cut surface extending in the second direction is a direction crossing the cut surface extending in the first direction, and a planar direction of the cut surface extending in the third direction is a direction crossing the cut surface extending in the first direction and the cut surface extending in the second direction.

The present invention also provides a method for cutting a biological tissue using the biological tissue cutting device according to the present invention, including: a fixing step of fixing a biological tissue on the stage; a first cutting step of cutting the biological tissue by the first cutting unit to form a cut surface extending in a first direction; and a second cutting step of cutting the biological tissue by the second cutting unit to form a cut surface extending in a second direction and a cut surface extending in a third direction, wherein a planar direction of the cut surface extending in the second direction is a direction crossing the cut surface extending in the first direction, and a planar direction of the cut surface extending in the third direction is a direction crossing the cut surface extending in the second direction and the cut surface extending in the third direction.

The present invention also provides a method for producing a tissue fragment, including: cutting a biological tissue by the cutting method according to the present invention.

The present invention also provides a method for regenerating a biological tissue, including the use of a tissue fragment obtained by the production method according to the present invention.

The present invention also provides a surgical operation method including the use of a tissue fragment obtained by the production method according to the present invention.

The present invention also provides a therapeutic method including the use of a tissue fragment obtained by the production method according to the present invention.

Effects of the Invention

The biological tissue cutting device of the present invention can produce a large number of tissue fragments easily and efficiently by performing the formation of cut surfaces extending in the first direction and the formation of cut surfaces extending in the second direction and cut surfaces extending in the third direction.

BRIEF DESCRIPTION OF DRAWINGS

FIG. 3A is a perspective view schematically showing a second cutting unit (Y and Z plane cutting unit) in the embodiment of the present invention. FIG. 3B is a plan view of a second cutting section in the second cutting unit. FIG. 3C is a plan view of a third cutting section in the second cutting unit.

FIG. 4A shows a first direction corresponding to a cutting direction by the first cutting unit. FIG. 4B is a schematic view showing the state where the biological tissue is cut in the first direction.

FIG. 5A shows a second direction and a third direction corresponding to cutting directions by the second cutting unit. FIG. 5B is a schematic view showing the state where the biological tissue is cut in the second direction and the third direction.

Figure 1:
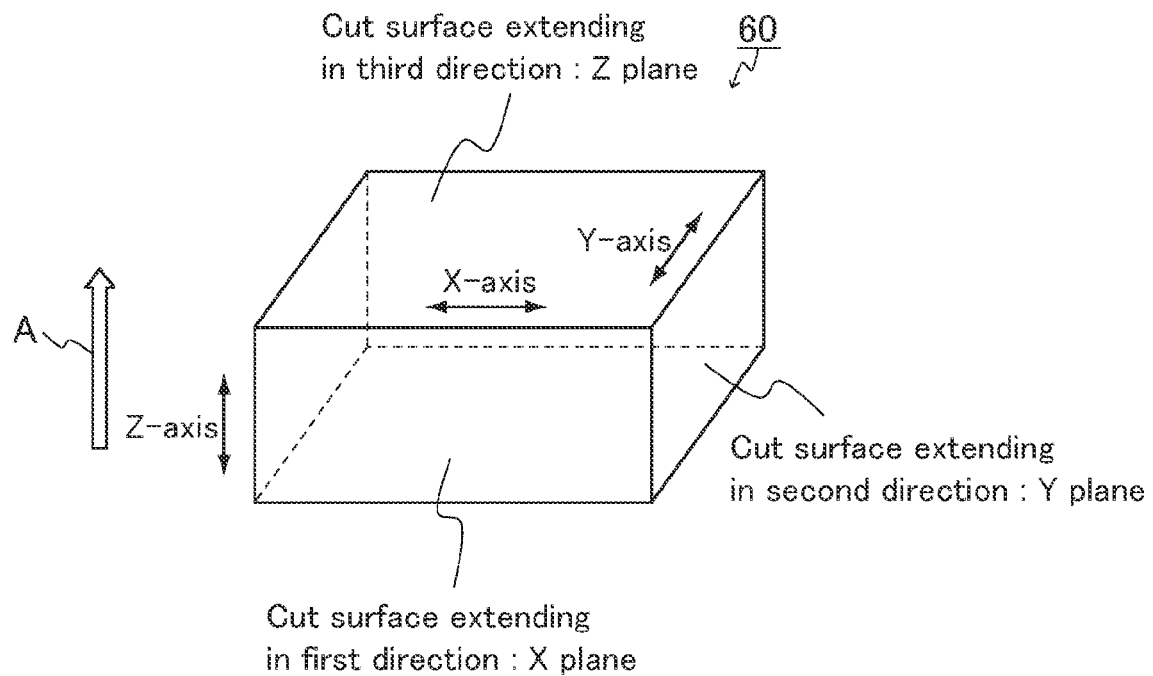
FIG. 1 is a perspective view schematically showing cut surfaces of a biological tissue in the present invention.

MODE FOR CARRYING OUT THE INVENTION (1) Biological Tissue Cutting Device

As described above, the biological tissue cutting device of the present invention is a biological tissue cutting device for producing a tissue fragment by cutting a biological tissue, including: a stage unit including a stage on which a biological tissue is fixed; a first cutting unit configured to form a cut surface extending in a first direction by cutting the biological tissue on the stage; and a second cutting unit configured to form a cut surface extending in a second direction and a cut surface extending in a third direction by cutting the biological tissue on the stage, wherein a planar direction of the cut surface extending in the second direction is a direction crossing the cut surface extending in the first direction, and a planar direction of the cut surface extending in the third direction is a direction crossing the cut surface extending in the first direction and the cut surface extending in the second direction.

According to the biological tissue cutting device of the present invention, for example, after the first cutting unit cuts the biological tissue to form the cut surface extending in the first direction, the second cutting unit can form the cut surface extending in the second direction and the cut surface extending in the third direction by a single operation, whereby a minute tissue fragment can be obtained. In the case where, for example, a cut surface extending in the second direction is formed and then a cut surface extending in the third direction is formed by separate operations of cutting the biological tissue, the biological tissue may fall down (collapse) during the formation of the cut surface extending in the third direction, which makes the cutting operation difficult. In contrast, according to the biological tissue cutting device of the present invention, a cut surface extending in the second direction and a cut surface extending in the third direction can be formed by subjecting the biological tissue to a single cutting operation by the second cutting unit. Thus, it is possible to avoid the above-described problem and improve the yield, for example. In the present invention, it should be interpreted that the term "section" used in various contexts is interchangeable with the term "mechanism", for example.

As described above, the second cutting unit can form a cut surface extending in the second direction and a cut surface extending in the third direction by a single process. In other words, the cut surface extending in the second direction and the cut surface extending in the third direction are formed simultaneously by simultaneous cutting, for example. In the present invention, the term "simultaneously" used regarding the formation of a cut surface extending in the second direction and a cut surface extending in the third direction means that, for example, they are formed by a single operation by the second cutting unit. The cutting and the formation of the cut surfaces themselves may be started exactly at the same time or at different times, for example. This can be set as appropriate according to the structure etc. of the second cutting section and the third cutting section to be described below, for example.

In the present invention, it is only necessary that the cut surface extending in the first direction, the cut surface extending in the second direction, and the cut surface extending in the third direction satisfy the above-described relationships, respectively. The planar direction of each of the cut surfaces can be defined as follows, relative to a surface of the stage on which the biological tissue is fixed, for example. Specifically, the cut surface extending in the first direction and the cut surface extending in the second direction of the biological tissue (biological sample) are both substantially perpendicular to the surface of the stage; the cut surface extending in the first direction is substantially perpendicular to the cut surface extending in the second direction; and the cut surface extending in the third direction of the biological tissue is substantially parallel to the surface of the stage.

As a specific example, FIG. 1 schematically shows a biological tissue fixed on a stage. In FIG. 1, the head of the arrow A indicates the upper direction when a biological tissue 60 is fixed on the stage. In FIG. 1, the cut surface extending in the first direction and the cut surface extending in the second direction are substantially perpendicular to the surface of the stage (not shown), and the cut surface extending in the third direction is substantially parallel to the surface of the stage. The cut surface extending in the first direction is, for example, a cut surface formed by cutting the biological tissue 60 in the X-axis direction with the biological tissue 60 viewed from above, and also is referred to as an "X plane". The cut surface extending in the second direction is, for example, a cut surface formed by cutting the biological tissue 60 in the Y-axis direction with the biological tissue 60 viewed from above, and also is referred to as a "Y plane". The cut surface extending in the third direction is, for example, a cut surface formed by cutting the biological tissue 60 in a direction perpendicular to the Z axis with the biological tissue 60 viewed transversely (viewed from the side of the biological tissue), and also is referred to as a "Z plane".

In the present invention, it is only necessary that the planar directions of the cut surface extending in the first direction, the cut surface extending in the second direction, and the cut surface extending in the third direction cross each other. The crossing angle is, for example, 90°±30°, 90°±20°, 90°±10°, or 90°±010°. Preferably, the planar directions are substantially orthogonal to each other or orthogonal to each other. Hereinafter, unless otherwise stated, the planar directions of the respective cut surfaces are not limited to those orthogonal to each other, and the description in this paragraph is applicable throughout the following descriptions.

In the biological tissue cutting device of the present invention, the biological tissue to be cut is not particularly limited, and may be a biological tissue used for the production of tissue fragments, for example. Specifically, the biological tissue to be cut may be a biological tissue to be used in regenerative medicine, a biological tissue to be used for cell preparation, or the like. Specific examples of the biological tissue include: cartilage; skin tissues; vascular tissues; liver tissues; membrane tissues such as periostea, synovial membranes, mucous membranes, and periodontal membranes; hormone-producing tissues such as the thyroid, the adrenal glands, and the prostate; nerves; tendons; fat; and muscles. When the tissue fragments are produced from the biological tissue to be used in regenerative medicine, the tissue fragments also can be referred to as tissue fragments for use in regenerative medicine, for example. When the tissue fragments are produced from the biological tissue to be used for cell preparation, the tissue fragments also can be referred to as tissue fragments for use in cell preparation, for example.

In the biological tissue cutting device of the present invention, the shape of the biological tissue fixed on the stage is not particularly limited, and may be a sheet-like shape, a block-like shape, or the like, for example. The size of the biological tissue is not particularly limited. The size of the biological tissue fixed on the stage may be such that: the lower limit of the thickness is, for example, 0.05 mm, 0.5 mm, or 1 mm; the upper limit of the thickness is, for example, 3 mm, 5 mm, or 10 mm; the range of the thickness is, for example, from 0.05 to 10 mm, from 0.5 to 5 mm, from 0.5 to 3 mm, or from 1 to 3 mm; the lower limit of the area is, for example, 50 mm$^2$, 100 mm$^2$, or 200 mm$^2$; the upper limit of the area is, for example, 2,500 mm$^2$, 5,000 mm$^2$, or 10,000 mm$^2$; and the range of the area is, for example, from 50 to 10,000 mm$^2$, from 100 to 5,000 mm$^2$, or from 200 to 2,500 mm$^2$.

The method for fixing the biological tissue on the stage is not particularly limited. For example, the biological tissue may be fixed on the stage with an adhesive. The adhesive is not particularly limited, and preferably is a medical adhesive such as, for example, an α-cyanoacrylate adhesive. The material of the surface of the stage on which the biological tissue is fixed is not particularly limited, and may be, for example: a polymer such as polycarbonate; or glass. The stage may be a microscope slide or the like, for example.

The shape of the tissue fragment obtained through cutting by the first cutting unit and the second cutting unit of the biological tissue cutting device of the present invention is not particularly limited, and may be a cubic shape, for example. The size of the tissue fragment is not particularly limited, and may be such that: the lower limit of the length of one side is, for example, 0.03 mm, 0.05 mm, 0.1 mm, or 0.2 mm; the upper limit of the length of one side is, for example, 1 mm, 2 mm, or 3 mm; and the range of the length of one side is, for example, from 0.03 to 3 mm, from 0.05 to 3 mm, from 0.1 to 2 mm, or from 0.2 to 1 mm.

In the biological tissue cutting device of the present invention, for example, the first cutting unit includes a first cutting section that cuts the biological tissue to form the cut surface extending in the first direction, and the second cutting unit includes a second cutting section that cuts the biological tissue to form the cut surface extending in the second direction and a third cutting section that cuts the biological tissue to form the cut surface extending in the third direction. In the second cutting unit, the second cutting section and the third cutting section are integrated in such a manner that, for example, the cut surface extending in the second direction and the cut surface extending in the third direction formed by the second cutting section and the third cutting section maintain a fixed angle. In each of the first cutting section, the second cutting section, and the third cutting section, the type of the cutting section is not particularly limited as long as it can cut biological tissues. Specifically, the cutting section may be a blade of a cutter, a knife, or the like.

The first cutting section in the first cutting unit and the second cutting section and the third cutting section in the second cutting unit will be described by way of example with reference to FIGS. 2 and 3.

Figure 2:
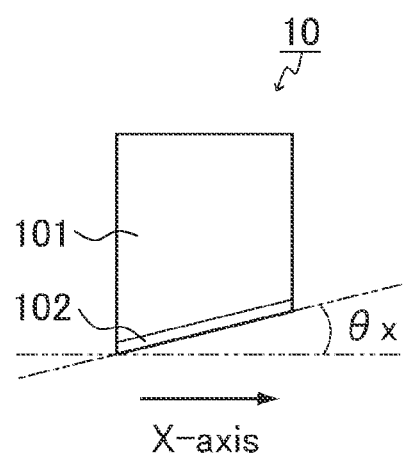
FIG. 2 is a plan view showing a first cutting section of a first cutting unit (X plane cutting unit) in the embodiment of the present invention.

FIG. 2 is a schematic side view showing an example of a first cutting section 10 in the first cutting unit. In FIG. 2, the first cutting section 10 has a blade 102 formed along the lower end of a main body 101. At the time of cutting a biological tissue by the first cutting section 10, the biological tissue is disposed ahead of the arrow and the first cutting section 10 is moved along the arrow direction, whereby the biological tissue is cut by the blade 102 to form a cut surface extending in the first direction. Assuming that the biological tissue has a horizontal surface, it is preferable that the blade 102 is an obliquely extending blade that forms a predetermined angle θx with the surface. It also can be said that the angle is an angle formed with the moving direction. When the angle θx is represented as sin θx, it preferably is such that, for example: the lower limit thereof is, for example, 1/200, 3/200, or 5/200; the upper limit thereof is, for example, 30/200, 50/200, or 80/200; and the range thereof is, for example, from 1/200 to 80/200, from 3/200 to 50/200, or from 5/200 to 30/200. The thickness of the blade 102 is such that: the lower limit thereof is, for example, 10 μm, 20 μm, or 30 μm; the upper limit thereof is, for example, 500 μm, 600 μm, or 850 μm; and the range thereof is, for example, from 10 to 850 μm, from 20 to 600 μm, or from 30 to 500 μm.

FIG. 3A is a perspective view showing an example of a second cutting unit 40. FIG. 3B is a plan view of a second cutting section 20 of the second cutting unit 40. FIG. 3C is a plan view of a third cutting section 30 of the second cutting unit 40. As shown in FIG. 3, the second cutting unit 40 includes a support 401, the second cutting section 20, and the third cutting section 30. The second cutting section 20 and the third cutting section 30 are mounted to the support 401, whereby they are integrated into one component as a whole. The second cutting section 20 has a blade 202 formed along the lower end of a main body 201. The third cutting section 30 has a blade 302 formed along an edge (edge on the left in FIG. 3A) of a main body 301. The planar direction of the blade 202 of the second cutting section 20 and the planar direction of the blade 302 of the third cutting section 30 are substantially perpendicular to each other, for example. Specifically, it also can be said that the blade of the second cutting section 20 and the blade of the third cutting section 30 are orthogonal to each other with the point of action as a boundary, for example. At the time of cutting the biological tissue by the second cutting unit 40, the biological tissue is disposed ahead of the arrow and the second cutting unit 40 is moved along the arrow direction, whereby the biological tissue is cut by the blade 202 to form a cut surface extending in the second direction and cut by the blade 302 to form a cut surface extending in the third direction.

Assuming that the biological tissue has a horizontal surface, it is preferable that the blade 202 of the second cutting section 20 is an obliquely extending blade that forms a predetermined angle θy with the surface. It also can be said that the angle is an angle formed with the moving direction. Also, assuming that the biological tissue has a horizontal surface, it is preferable that the blade 302 of the third cutting section 30 moves in parallel to the surface and that the blade 302 is an obliquely extending blade that forms a predetermined angle θz with the moving direction. When the angle θy or θz is represented as sin θy or sin θz, it preferably is such that, for example: the lower limit thereof is, for example, 1/200, 3/200, or 5/200; the upper limit thereof is, for example, 30/200, 50/200, or 80/200; and the range thereof is, for example, from 1/200 to 80/200, from 3/200 to 50/200, or from 5/200 to 30/200.

The thickness of the blade 202 of the second cutting section is such that: the lower limit thereof is, for example, 10 μm, 20 μm, or 30 μm; the upper limit thereof is, for example, 500 μm, 600 μm, or 850 μm; and the range thereof is, for example, from 10 to 850 μm, from 20 to 600 μm, or from 30 to 500 μm. The thickness of the blade 302 of the third cutting section is such that: the lower limit thereof is, for example, 10 μm, 20 μm, or 30 μm; the upper limit thereof is, for example, 1500 μm, 2000 μm, or 3000 μm; and the range thereof is, for example, from 10 to 3000 μm, from 20 to 2000 μm, or from 30 to 1500 μm.

Preferably, the blade of the first cutting section and the blade of the second cutting section are relatively thin as compared with the blade of the third cutting section, because, for example, they can be inserted into a biological tissue more easily and the biological tissue after being subjected to the cutting can maintain its original shape as a whole more easily. In particular, for example, when the blade of the first cutting section is relatively thin as compared with the blade of the third cutting section, streaks of cut surfaces (e.g., slits shown in FIG. 5A) are aligned more neatly, thus improving the operability in the second cutting step and the third cutting step. The blade of the third cutting section cuts the biological tissue from the top to the bottom as if it scrapes off layers one by one so as to form Z planes, and collects the layers, for example. Thus, the thickness of the blade of the third cutting section is not particularly limited. The blade of the third cutting section may be relatively thick as compared with the blade of the first cutting section and the blade of the second cutting section, so as to allow the blade to be sharpened to improve the cutting quality, for example.

FIGS. 2 and 3 are directed to an example where the first cutting section, the second cutting section, and the third cutting section have single-edged blades. It is to be noted, however, that the present invention is not limited thereto, and the first cutting section, the second cutting section, and the third cutting section may have double-edged blades, for example. The first cutting section may have a single-edged or double-edged round blade, for example.

The biological tissue cutting device of the present invention may further include, for example, a first movement control section that moves the first cutting section in the first cutting unit, a second movement control section that moves the second cutting section and the third cutting section in the second cutting unit, and/or a stage movement control section that moves the stage on which the biological tissue is fixed. The biological tissue cutting device of the present invention may include any one or two of these control sections, or may include all of them, for example. Each of the control section is not particularly limited, and may be, for example, a section that utilizes a ratchet mechanism, a section that utilizes a cam mechanism, or the like.

The biological tissue cutting device of the present invention can produce a plurality of tissue fragments from one biological tissue fixed on the stage by, for example, repeatedly cutting the biological tissue by the first cutting unit and the second cutting unit. In this case, for example, the above-described repetition of the cutting operations can be controlled with the use of any one of the first movement control section, the second movement control section, and the stage movement control section or any combination of these control sections. Each of the cutting sections may be operated manually as will be described below, or may be operated electrically (automatically), for example. The cutting sections are not particularly limited by the method for operating them.

As a first example, the biological tissue cutting device of the present invention including the first movement control section will be described. The biological tissue cutting device of this first example is configured so that, for example, the first cutting unit includes the first cutting section that cuts a biological tissue to form a cut surface extending in the first direction and a first movement control section that moves the first cutting section. In this case, the first movement control section moves the first cutting section from a cutting start position to a cutting end position of the biological tissue and then to a new cutting start position, for example. The movement from the cutting start position to the cutting end position means one cutting operation achieved by the movement of the cutting section in one direction with respect to the biological tissue (the same applies hereinafter). As a result, the first cutting section is set at the new cutting start position. The first movement control section can cut the biological tissue by subsequently moving the first cutting section from the new cutting start position to a cutting end position.

It is preferable that, after the first movement control section has moved the first cutting section from the cutting start position to the cutting end position, the first movement control section moves the first cutting section away from the biological tissue and then to the new cutting start position, for example. By moving the first cutting section to the new cutting start position after moving the first cutting section away from the biological tissue, the cut surface formed by the first cutting section can be kept neater, for example. The method for moving the first cutting section away from the biological tissue is not particularly limited. When the movement of the first cutting section from the cutting start position to the cutting end position is movement from the near side to the far side of the biological tissue, the first movement control section can move the first cutting section away from the biological tissue by, for example, moving the first cutting section to the cutting end position and then pushing the first cutting section out from the biological tissue. On the other hand, when the movement of the first cutting section from the cutting start position to the cutting end position is movement from the far side to the near side of the biological tissue, the first movement control section can move the first cutting section away from the biological tissue by, for example, moving the first cutting section to the cutting end position and then pulling the first cutting section out from the biological tissue.

When the first movement control section moves the first cutting section to the new cutting start position, the first movement control section may move the first cutting section from the cutting end position to the new cutting start position directly, or may return the first cutting section from the cutting end position to the cutting start position and then move the first cutting section to the new cutting start position, for example.

Figure 4A:
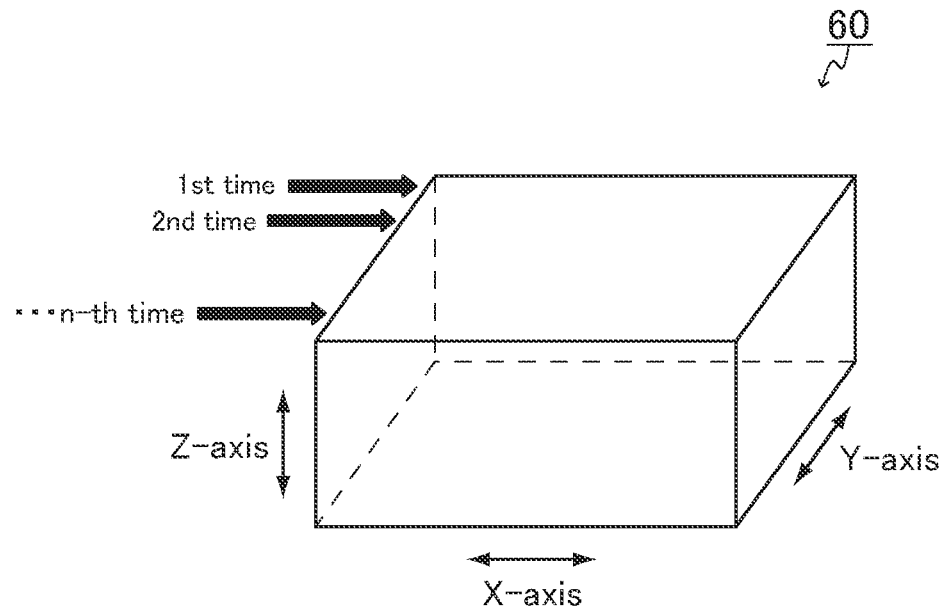
FIGS. 4A and 4B are schematic views of a biological tissue in the embodiment of the present invention.
Figure 4B:
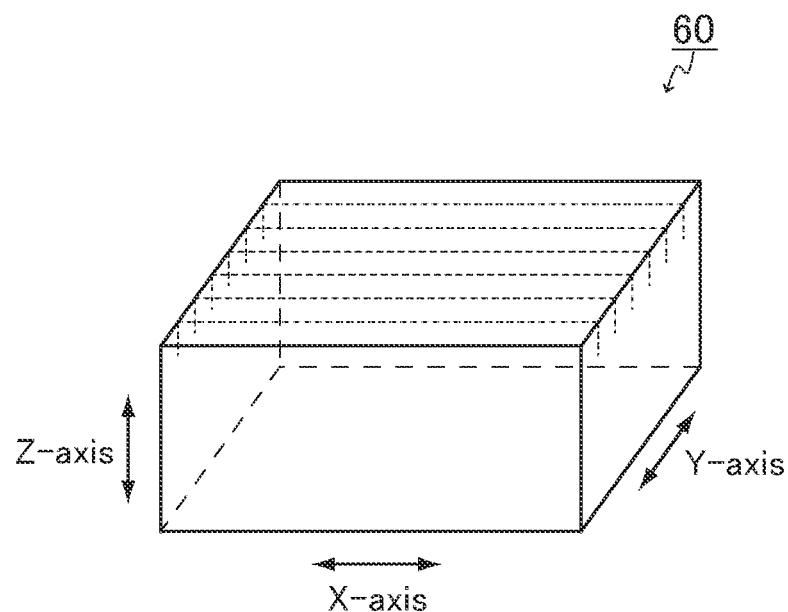

As a specific example, FIGS. 4A and 4B schematically show a biological tissue fixed on the stage. As shown in FIG. 4A, the first cutting section is set at a first cutting start position of the biological tissue 60 on the stage. Then, the biological tissue 60 is subjected to a first cutting operation in the X-axis direction with the biological tissue 60 viewed from above. After the first cutting section has been moved to the cutting end position for the first cutting operation, the first cutting section is moved to a new cutting start position for a second cutting operation. Then, the second cutting operation in the X-axis direction is performed. By repeating this step to a total of n times (n is a positive integer), the cutting operation in the X-axis direction is performed a plurality of times, and a plurality of cut surfaces extending in the first direction (X planes) are formed, as shown in FIG. 4B. In the present invention, the first cutting unit also is referred to as an "X plane cutting unit", and the first cutting section also is referred to as an "X plane cutting section", because they can form the X plane.

The cutting operation in the X-axis direction can be performed a plurality of times by moving the first cutting section in the X-axis direction. The depths achieved by this series of cutting operations preferably are set to be substantially the same. The depth is not particularly limited, and may be, for example, the length of one side of a tissue fragment to be obtained finally. As to this length, reference can be made to conditions to be described below.

As a second example, the biological tissue cutting device of the present invention including the second movement control section will be described. The biological tissue cutting device of this second example is configured so that, for example, the second cutting unit includes: a second cutting section that cuts the biological tissue to form a cut surface extending in the second direction; a third cutting section that cuts the biological tissue to form a cut surface extending in the third direction; and a second movement control section that moves the second cutting section and the third cutting section simultaneously, and the second cutting section and the third cutting section are integrated in such a manner that the cut surface extending in the second direction and the cut surface extending in the third direction formed by the second cutting section and the third cutting section maintain a fixed angle. In this case, the second movement control section moves the second cutting section and the third cutting section simultaneously from the cutting start position to the cutting end position of the biological tissue, for example. At this time, it is preferable that, for example, the cutting direction of the blade of the second cutting section is aligned with the planar direction of a cut surface extending in the second direction and that the cutting direction the blade of the third cutting section is aligned with the planar direction of a cut surface extending in the third direction. With this configuration, for example, by moving the second cutting section and the third cutting section in a direction that is parallel to the Y-axis direction and perpendicular to the Z-axis direction, the biological tissue can be cut so as to form a cut surface extending in the second direction and a cut surface extending in the third direction simultaneously.

It is preferable that the second movement control section moves the second cutting section and the third cutting section from the cutting start position to the cutting end position and then to a new cutting start position. As a result, the second cutting section is set in the new cutting start position. The second movement control section can cut the biological tissue by subsequently moving the second cutting section from the new cutting start position to a cutting end position.

After the second movement control section has moved the second cutting section and the third cutting section from the cutting start position to the cutting end position, the second movement control section may move the second cutting section and the third cutting section away from the biological tissue and then to the new cutting start position, for example. By moving the second cutting section and the third cutting section to the cutting start position after moving the second cutting section and the third cutting section away from the biological tissue, the cut surface formed by the second cutting section and the cut surface formed by the third cutting section can be kept neater, for example. The method for moving the second cutting section away from the biological tissue is not particularly limited. When the movement of the second cutting section from the cutting start position to the cutting end position is movement from the near side to the far side of the biological tissue, the second movement control section can move the second cutting section and the third cutting section away from the biological tissue by, for example, moving them to the cutting end position and then pushing them out from the biological tissue. On the other hand, when the movement of the second cutting section from the cutting start position to the cutting end position is movement from the far side to the near side of the biological tissue, the second movement control section can move the second cutting section and the third cutting section away from the biological tissue by, for example, moving them to the cutting end position and then pulling them out from the biological tissue.

After the second movement control section has moved the second cutting section and the third cutting section from the cutting start position to the cutting end position, the second movement control section may move the second cutting section and the third cutting section from the cutting end position to the cutting start position along the path, move them away from the biological tissue, and then move them to the new cutting start position, for example.

When the second movement control section subsequently moves the second cutting section and the third cutting section to the new cutting start position, the second movement control section may move the second cutting section and the third cutting section from the cutting end position to the new cutting start position directly, or may return the second cutting section and the third cutting section from the cutting end position to the cutting start position and then move them to the new cutting start position, for example. Then, by moving the second cutting section and the third cutting section from the new cutting start position to a cutting end position, it is possible to cut the biological tissue.

Figure 5A:
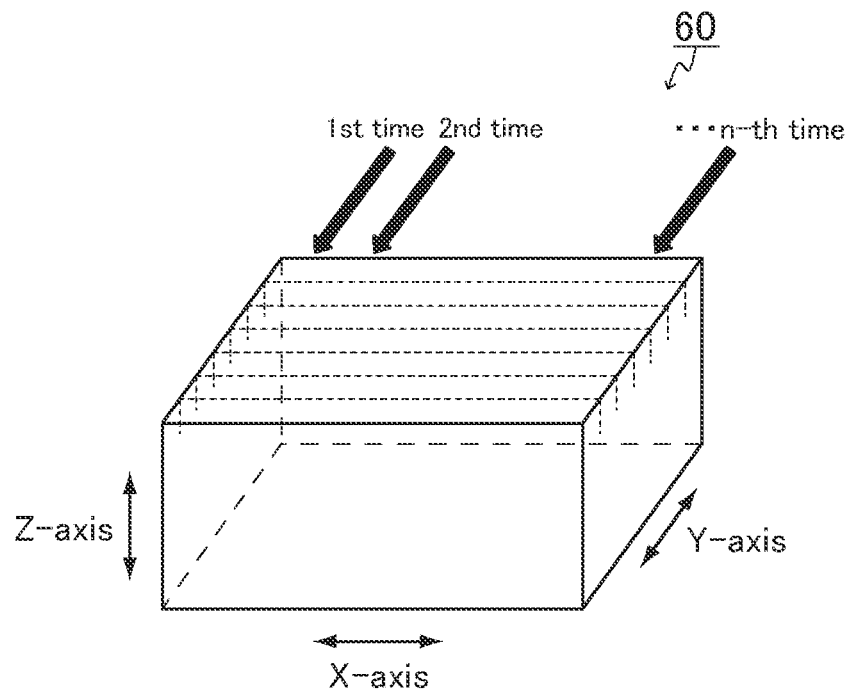
FIGS. 5A and 5B are schematic views showing the biological tissue in the embodiment of the present invention.
Figure 5B:
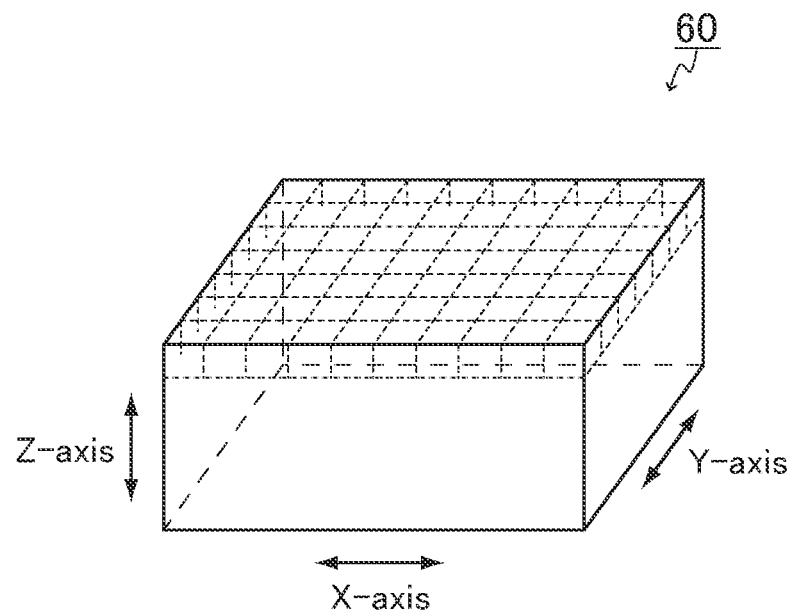

As a specific example, FIGS. 5A and 5B schematically show a biological tissue fixed on the stage. As shown in FIG. 5A, the second cutting section and the third cutting section are set at a first cutting start position of the biological tissue 60 on the stage. Then, the biological tissue 60 is subjected to a first cutting operation in the Y-axis direction (the direction perpendicular to the Z axis) with the biological tissue 60 viewed from above. After the second cutting section and the third cutting section have been moved to the cutting end position for the first cutting operation, the second cutting section and the third cutting section are moved to a cutting start position for a second cutting operation. Then, the second cutting operation in the Y-axis direction is performed. By repeating this step to a total of n times (n is a positive integer), cutting in the Y-axis direction is performed a plurality of times, as shown in FIG. 5B. As a result, cut surfaces extending in the second direction (Y plane) and cut surfaces extending in the third direction (Z plane) are formed, whereby a plurality of tissue fragments defined by cut surfaces extending in the first direction (X plane), cut surfaces extending in the second direction (Y plane), and cut surfaces extending in the third direction (Z plane) can be produced. In the present invention, the second cutting unit also is referred to as a "Y and Z plane cutting unit" because it can form the Y plane and the Z plane. The second cutting section also is referred to as a "Y plane cutting section", and the third cutting section also is referred to as a "Z plane cutting section".

When cut surfaces extending in the first direction, the second direction, and the third direction are formed for a predetermined layer in the height direction (Z-axis direction) of the biological tissue in the above-described manner, tissue fragments obtained by cutting the layer are gathered between the surface of the second cutting section and the surface of the third cutting section in the second cutting unit, for example. Thus, in the biological tissue on the stage, for example, the tissue fragments obtained by the cutting are removed to expose a new surface. Accordingly, for example, by setting the first cutting section in the first cutting unit and the second cutting section and the third cutting section in the second cutting unit at, e.g., a position lower than the removed layer and cutting a new layer in the same manner, it is possible to subsequently produce tissue fragments.

As a third example, the biological tissue cutting device of the present invention including the stage movement control section will be described. The biological tissue cutting device of this third example is configured so that, for example, the stage unit further includes the stage movement control section. Specifically, the stage movement control section moves the stage in at least one of an upper direction, a lower direction, and a planar direction relative to a surface of the stage on which the biological tissue is fixed, for example. The stage movement control section may move the stage in only one of these directions, any two of these directions, or all the three directions, for example.

In the first example described above, the first cutting section is moved so as to form a cut surface extending in the first direction. In the present example, the biological tissue on the stage may be cut by the first cutting section by moving the stage, instead of moving the first cutting section. Also, the biological tissue on the stage may be cut by the second cutting section and the third cutting section by moving the stage, instead of moving the second cutting section and the third cutting section.

In the biological tissue cutting device of the present invention, it is preferable that, for example, each of components excluding the first cutting unit, the second cutting unit, and the stage on which a tissue to be cut is placed is formed of a sterilizable material. Specific examples of the sterilizable material include materials meeting sanitary specifications, with resistance to high temperature and high pressure so as to allow autoclave sterilization. It is desirable that the first cutting unit, the second cutting unit, and the stage are disposable and replaced for each patient, because this can further reduce the possibility of contamination and infection between individuals, for example.

The biological tissue cutting device of the present invention may be of a separate type in which the first cutting unit and the second cutting unit are provided as separate components, or may be of an integrated type in which the first cutting unit and the second cutting unit are disposed in a single component, for example.

The separate type device as the former is a device in which the first cutting unit and the second cutting unit are provided as separate components, as described above, and the first cutting unit and the second cutting unit each include a stage mounting section to which the stage is mounted, for example. In this case, for example, the stage is mounted to the stage mounting section in the first cutting unit, and the first cutting unit cuts the biological tissue to form a cut surface extending in the first direction. Thereafter, the stage is detached from the first cutting unit and mounted to the second cutting unit. The second cutting unit then cuts the biological tissue to form a cut surface extending in the second direction and a cut surface extending in the third direction.

The integrated device as the latter is configured so that the first cutting unit and the second cutting unit are disposed in a single component, as described above. At least one of the stage, the first cutting unit, and the second cutting unit is detachable.

In the following, as the biological tissue cutting device of the present invention, the separate type device and the integrated device will be described by way of example. It is to be noted, however, that the present invention is not limited to these illustrative embodiments by any means. Unless otherwise stated, the descriptions in one embodiment are incorporated by reference into the other embodiment. In the drawings to be described below, the same components are given the same reference numerals.

First Embodiment

As a first embodiment, an example of the separate type device of the present invention will be described with reference to FIGS. 6 to 7. The separate type device of the present embodiment is a device in which a first cutting unit and a second cutting unit are provided as separate components. Unless otherwise stated, the descriptions regarding the first cutting unit and the second cutting unit are incorporated by reference into each other.

Figure 6:
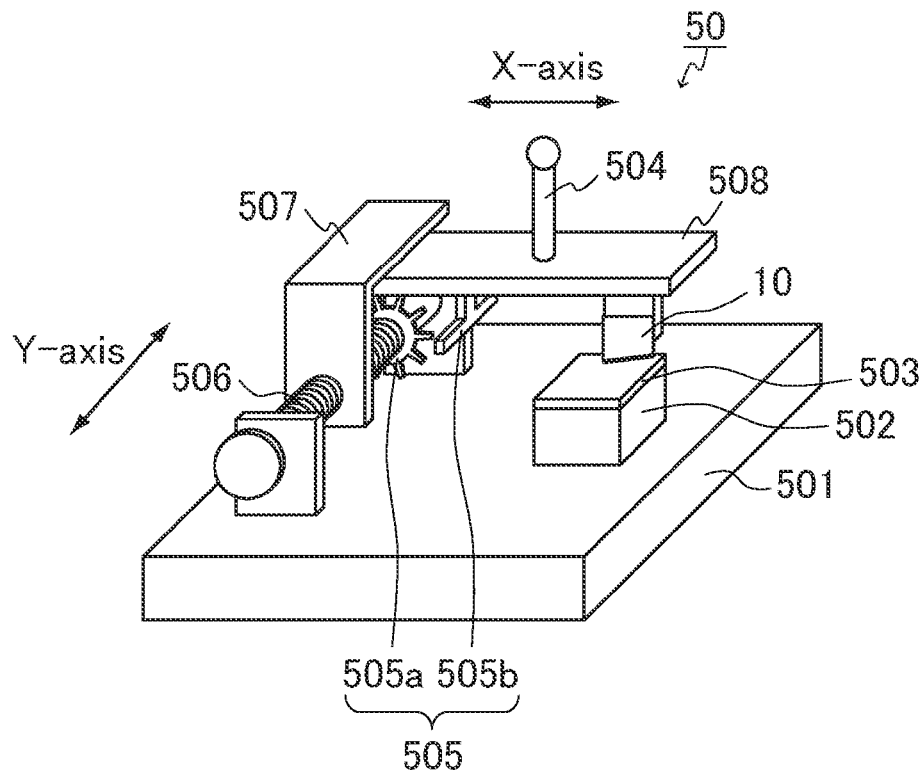
FIG. 6 is a perspective view schematically showing a first cutting unit (X plane cutting unit) in another embodiment of the present invention.

FIG. 6 is a perspective view schematically showing a first cutting unit (X plane cutting unit) 50. As shown in FIG. 6, the first cutting unit 50 includes: a substrate 501; a first cutting section 10; and a stage unit. In the first cutting unit 50, the first cutting section 10 is set in such a manner that the relationship between the direction of the blade 102 and the X-axis direction is as described above with reference to FIG. 2.

The stage unit includes: a stage 503 on which a biological tissue is fixed; and a stage mounting section 502 on which the stage 503 is mounted. On the stage mounting section 502 disposed on the substrate 501, the stage 503 is mounted in a detachable manner. The stage 503 may be fixed on the stage mounting section 502 using an engaging tool(s) such as a screw(s) or a plunger screw(s), for example. By using the engaging tool, for example, the biological tissue can be positioned more reliably during cutting operations.

The first cutting unit 50 further may include, for example, a height adjustment section that adjusts the height of the stage 503. As described above, cutting of a biological tissue fixed on the stage 503 is started from a surface layer on the upper side, and the surface layer after the cutting is removed, for example. On this account, it is preferable that the height of the stage 503 can be adjusted by the height adjustment section so that a newly exposed surface layer can be cut. Also, by adjusting the positional relationship between the biological tissue fixed on the stage 503 and the blade 102 of the first cutting section 10 through the adjustment of the height of the stage 503, it is possible to adjust the cutting depth (cutting dimension) of the biological tissue, for example. Such adjustment allows, for example, slits formed on the biological tissue by the first cutting section 10 to have a sufficient depth, thus realizing a sufficient yield. Also, in the case where the biological tissue is fixed with an adhesive or the like, the above-described adjustment can prevent the adhesive layer from being cut, for example, so that contamination of the obtained tissue fragments with the adhesive layer and also the collapse of the biological tissue caused by the cutting of the adhesive layer can be prevented sufficiently.

The height adjustment section is not particularly limited, and may be, for example a bolt type adjuster, a dial type adjuster, a screw type adjuster, a ratchet type adjuster, or the like. The height adjustment section may be provided in the stage mounting section 502, for example.

The first cutting section 10 is coupled to a first movement control section disposed on the substrate 501. The first movement control section includes: a section that moves the first cutting section 10 in the X-axis direction; and a section that moves the first cutting section 10 in the Y-axis direction. By providing the first movement control section and moving the first cutting section 10 in the X-axis direction and the Y-axis direction as described above, X plane formation can be performed repeatedly a plurality of times for the biological tissue fixed on the stage 503, whereby X planes aligned in parallel to each other are formed, for example.

The X-axis direction movement section as the former will be described. The first cutting section 10 is mounted to a slidable mounting plate 508, and a handle 504 is fixed on the mounting plate 508. This handle 504 serves as the X-axis direction movement section.

The Y-axis direction movement section as the latter will be described. The movement section includes: a ratchet 505 including a ratchet gear 505a and a ratchet pawl 505b; a feed screw 506; and a feed nut 507. The ratchet pawl 505b is fixed on the mounting plate 508, which is described above in connection with the X-axis direction movement section. The ratchet gear 505a and the feed nut 507 are each threadedly engaged with the feed screw 506.

The first movement control section moves the first cutting section 10 in the X-axis direction and the Y-axis direction in the following manner, for example. First, by moving the handle 504 in the X-axis direction, the first cutting section 10 mounted to the mounting plate 508 can be moved in the X-axis direction, whereby the biological tissue fixed on the stage 503 is cut to form an X plane. Specifically, by moving the handle 504 from the ratchet 505 side to the opposite side (from left to right in FIG. 6) along the X-axis direction, the first cutting section 10 is moved from a cutting start position to a cutting end position, thereby forming a slit extending in the X-axis direction on the biological tissue. Thus, an X plane is formed in the biological tissue. Next, by pushing the handle 504 in the X-axis direction so as to return the handle 504 from the opposite side to the ratchet 505 side (from right to left in FIG. 6), the ratchet pawl 505b fixed on the mounting plate 508 pushes the ratchet gear 505a. As a result, the feed screw 506 threadedly engaged with the ratchet gear 505a is rotated by one pitch, which in turn causes the feed nut 507 threadedly engaged with the feed screw 506 to move in the Y-axis direction by a fixed movement interval (to the near side in FIG. 6). The feed nut 507 moves in conjunction with the mounting plate 508. Thus, by these movements, the first cutting section 10 mounted to the mounting plate 508 can be moved in the Y-axis direction. As described above, by a single reciprocal movement of the first cutting section 10 in the X-axis direction, the biological tissue is cut once, and also, the position of the first cutting section 10 can be moved in the Y-axis direction for subsequent cutting.

The above-described pitch is not particularly limited, and can be adjusted according to the groove structure of the feed screw, for example. The movement interval of the first cutting section 10 in the Y-axis direction corresponds to, for example, cut spacing in the X plane formation by the first cutting section. For example, the width of the cut spacing can be determined freely by changing the pitch of the feed screw 506 in increments of 45°.

When the first movement control section causes the reciprocal movement of the first cutting section 10 in the X-axis direction, it is preferable that the first cutting section 10 is moved from the cutting start position to the cutting end position as described above, and then moved to a new cutting start position with the tip of the blade 102 being away from the biological tissue. In this case, the first cutting unit 50 further may include, for example, a section that moves the first cutting section away from the biological tissue when the first cutting section 10 reaches a cutting end position. The section is not particularly limited, and may be a cam mechanism such as a grooved cam, for example. Specifically, for example, the cam mechanism may include a cam that moves in conjunction with the first cutting section 10, so that, when the first cutting section 10 reaches a cutting end position, the first cutting section 10 is moved upward along the cam so as to be away from the biological tissue, whereas, when the first cutting section 10 reaches a new cutting start position, the first cutting section 10 is moved downward along the cam to reach the biological tissue.

Figure 7:
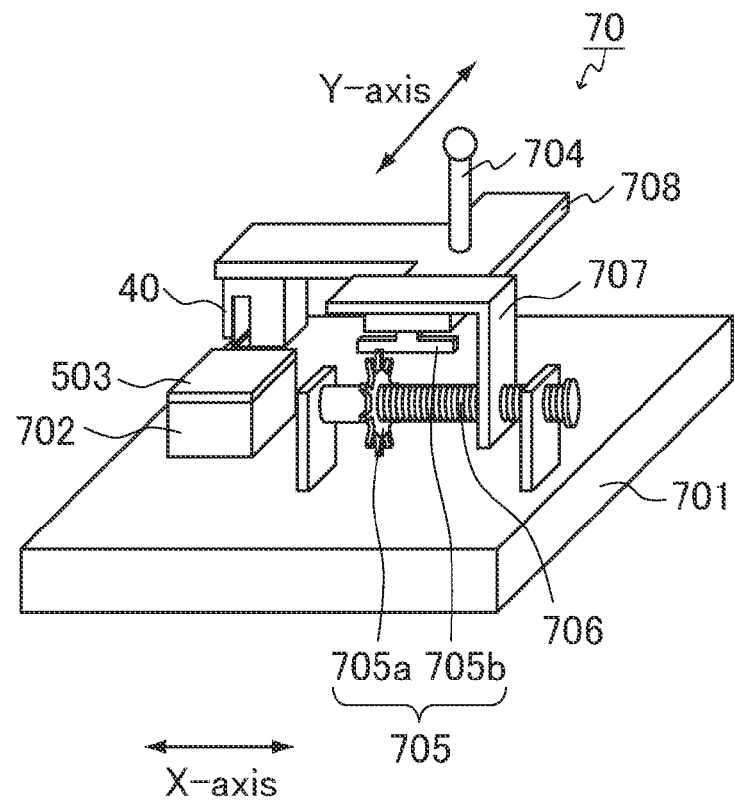
FIG. 7 is a perspective view schematically showing a second cutting unit (Y and Z plane cutting unit) in an embodiment of the present invention.

FIG. 7 is a perspective view schematically showing a second cutting unit (Y and Z plane cutting unit) 70. As shown in FIG. 7, the second cutting unit 70 includes: a substrate 701; a unit 40 including a second cutting section 20 and a third cutting section 30; and a stage unit. In the second cutting unit 70, the second cutting section 20 and the third cutting section 30 are set in such a manner that the relationship between the direction of blade 202 of the second cutting section 20 and the Y-axis direction and the relationship between the direction of the blade 302 of the third cutting section 30 and the Y-axis direction are as described above with reference to FIG. 3.

The stage unit includes: a stage 503 on which a biological tissue is fixed; and a stage mounting section 702 on which the stage 503 is mounted. On the stage mounting section 702 disposed on the substrate 701, the stage 503 is mounted in a detachable manner. After the biological tissue has been subjected to the cutting by the first cutting unit 50 shown in FIG. 6 as described above, the biological tissue after the cutting is detached from the first cutting unit 50 together with the stage 503. The stage 503 thus detached is mounted on the stage mounting section 702 of the second cutting unit 70 with the biological tissue after the cutting being fixed on the stage 503. At this time, the stage 503 is set in such a manner that the relationships between the blades 202 and 302 of the second cutting section 20 and the third cutting section 30 and each of the axis directions in the biological tissue are as described above with reference to FIGS. 3 and 5.

The second cutting unit 70 also further may include, for example, a height adjustment section that adjusts the height of the stage 503, as in the case of the above-described first cutting unit 50. As described above, cutting of a biological tissue fixed on the stage 503 is started from a surface layer on the upper side, and the surface layer after the cutting is removed, for example. On this account, it is preferable that the height of the stage 503 can be adjusted by the height adjustment section so that a newly exposed surface layer can be cut. Also, by adjusting the positional relationship of the biological tissue fixed on the stage 503 with the blade 202 of the second cutting section 20 and the blade 302 of the third cutting section 30 through the adjustment of the height of the stage 503, it is possible to adjust the cutting depth (cutting dimension) of the biological tissue, for example. Such adjustment allows, for example, slits formed on the biological tissue by the second cutting section 20 and the third cutting section 30 to have a sufficient depth, thus realizing a sufficient yield. Also, in the case where the biological tissue is fixed with an adhesive or the like, the above-described adjustment can prevent the adhesive layer from being cut, for example, so that contamination of the obtained tissue fragments with the adhesive layer and also the collapse of the biological tissue caused by the cutting of the adhesive layer can be prevented sufficiently.

The unit 40 including the second cutting section 20 and the third cutting section 30 is coupled to a second movement control section disposed on the substrate 701. The second movement control section includes: a section that moves the second cutting section 20 and the third cutting section 30 in the Y-axis direction; and a section that moves the second cutting section 20 and the third cutting section 30 in the X-axis direction. By providing the second movement control section and moving the second cutting section 20 and the third cutting section 30 in the Y-axis direction and the X-axis direction as described above, Y and Z plane formation can be performed repeatedly a plurality of times for the biological tissue fixed on the stage 503, whereby Y planes and Z planes both aligned in parallel to each other are formed, for example.

The Y-axis direction movement section as the former will be described. The second cutting section 20 (e.g., the second cutting unit 40 in FIG. 7) is mounted to a slidable mounting plate 708, and a handle 704 is fixed on the mounting plate 708. The handle 704 serves as the Y-axis direction movement section.

The X-axis direction movement section as the latter will be described. The movement section includes: a ratchet 705 including a ratchet gear 705a and a ratchet pawl 705b; a feed screw 706; and a feed nut 707. The ratchet pawl 705b is fixed on the mounting plate 708, which is described above in connection with the y-axis direction movement section. The ratchet gear 705a and the feed nut 707 are each threadedly engaged with the feed screw 706.

The second movement control section moves the second cutting section 20 and the third cutting section 30 in the Y-axis direction and the X-axis direction in the following manner, for example. First, by moving the handle 704 in the X-axis direction, the second cutting section 20 and the third cutting section 30 mounted to the mounting plate 708 can be moved in the Y-axis direction, whereby the biological tissue fixed on the stage 503 is cut to form a Y plane and a Z plane. Specifically, by pushing the handle 704 in the Y-axis direction so as to move the handle 704 from the ratchet 705 side to the opposite side (from the near side to the far side on the plane of FIG. 7), the second cutting section 20 and the third cutting section 30 are moved from a cutting start position to a cutting end position, whereby a Y plane and a Z plane are formed in the biological tissue. Next, by moving the handle 704 in the Y-axis direction so as to return from the opposite side to the ratchet 705 side (from the far side to the near side on the plane of FIG. 7), the ratchet pawl 705b fixed to the mounting plate 708 pushes the ratchet gear 705a. As a result, the feed screw 706 threadedly engaged with the ratchet gear 705a is rotated by one pitch, which in turn causes the feed nut 707 threadedly engaged with the feed screw 706 to move in the X-axis direction by a fixed movement interval (to right in FIG. 7). The feed nut 707 moves in conjunction with the mounting plate 708. Thus, by these movements, the second cutting section 20 and the third cutting section 30 mounted to the mounting plate 708 can be moved in the X-axis direction. As described above, by a single reciprocal movement of the second cutting section 20 and the third cutting section 30 in the Y-axis direction, the biological tissue is cut once, and also, the positions of the second cutting section 20 and the third cutting section 30 can be moved in the X-axis direction for subsequent cutting.

When the biological tissue is cut by the second cutting unit 70, a plurality of tissue fragments are produced as described above. The tissue fragments produced by the cutting may be gathered on the back (upper surface) of the third cutting section 30 in the second cutting unit 70, for example.

The method for cutting a biological tissue to produce tissue fragments using the separate type device of the first embodiment will be described by way of example. It is to be noted, however, that the present invention is not limited to this illustrative example.

(First Step)

First, a biological tissue is set on the stage 503. Specifically, for example, a microscope slide is used as the stage, and the biological tissue is caused to adhere to the center of a sample receiving part of the microscope slide. Then, the microscope slide is set on the stage mounting section 502. The microscope slide, for example, is fixed on the stage mounting section 502 by inserting a position fixing plunger screw(s) into the stage mounting section 502.

(Second Step)

Then, for cutting in the X-axis direction by the first cutting unit 50, the cutting dimension in the Z-axis direction (i.e., the cutting depth) is set. The cutting dimension can be adjusted by, for example, moving the stage 503 in the Z-axis direction by the height adjustment section of the stage.

(Third Step)

Next, the handle 504 of the first cutting unit 50 is moved from the ratchet side to the stage unit side (from left to right in FIG. 6) to complete the right moving stroke. As a result, a slit extending in the X-axis direction is formed on the biological tissue by the first cutting section 10, whereby an X plane is formed. When the right moving stroke of the handle 504 toward the stage unit side comes to a stroke end (one end point in the operable range of the first cutting section 10), the first cutting section 10 moving along the grooved cam is moved upward so as to be away from the biological tissue. Thus, at the same time with the completion of the cutting to form the X plane of the first row, the first cutting section 10 reaches the stroke end.

(Fourth Step)

The handle 504 of the first cutting unit 50 is returned toward the original position (from right to left in FIG. 6). At this time, the first cutting section 10 is moved along the grooved cam in the state where the first cutting section 10 is lifted upward as described above. When the left moving stroke of the handle 504 toward the ratchet side comes to a stroke end (the other end point in the operable range of the first cutting section 10), the ratchet pawl 505b pushes the ratchet gear 505a to rotate the feed screw 506 by one pitch. When the handle 504 comes to the stroke end after the completion of this movement, the first cutting section 10 is moved downward along the grooved cam to reach the biological tissue. The first cutting section 10 is set at a cutting start position for formation of an X plane of the next row, so that it is in the state ready for the start of a new cutting operation.

(Fifth Step)

When the cutting in the X-axis direction is completed after repeating the first to fourth steps, the position fixing plunger screw is pulled out from the stage mounting section 502, and the stage 503 is taken out from the first cutting unit 50 with the biological tissue being fixed thereon. Then, the stage 503 taken out from the first cutting unit 50 is mounted to the stage mounting section 702 of the second cutting unit 70 in the same manner. At this time, the stage 503 is mounted in such a manner that the X-axis, the Y-axis, and the Z-axis in the biological tissue are aligned with the cutting directions by the second cutting section 20 and the third cutting section 30 in the second cutting unit 70.

(Sixth Step)

Next, by moving the handle 704 of the second cutting unit 70 forward along the Y-axis direction from the ratchet side to the opposite side (from the near side to the far side on the plane of FIG. 7), the second cutting section 20 and the third cutting section 30 are moved simultaneously. By this operation, the biological tissue is cut further, whereby tissue fragments are produced.

(Seventh Step)

When the handle 704 of the second cutting unit 70 comes to a stroke end (one end point in the operable range of the second cutting section 20 and the third cutting section 30) in the forward direction, the handle 704 is moved in the direction opposite to the forward direction. Then, when the handle 704 comes to a stroke end in the opposite direction (the other end point in the operable range of the second cutting section 20 and the third cutting section 30), the ratchet pawl 705b pushes the ratchet gear 705a to rotate the feed screw 706 by one pitch. Tissue fragments are produced by repeating this operation to complete cutting by the second cutting section 20 and the third cutting section 30. By setting an appropriate size for this operation, it is possible to produce tissue fragments with desired dimensions.

(Eighth Step)

The tissue fragments produced by the cutting are gathered on, for example, a side surface of the second cutting section 20 and an upper surface of the third cutting section 30 as if these tissue fragments adhere thereto. Thus, it is possible to collect the tissue fragments in a sample receiving bucket by rinsing the second cutting section 20 and the third cutting section 30 with a solvent such as physiological saline, for example.

The first cutting section 10, the second cutting section 20, and the third cutting section 30 may be detached and replaced with new ones after the completion of the cutting, for example.

Second Embodiment

As a second embodiment, an example of the integrated biological tissue cutting device of the present invention will be described with reference to the drawings.

According to the second embodiment, the first cutting unit and the second cutting unit, which are provided as separate components in the first embodiment, are included in a single component, and the stage is shared by the first cutting unit and the second cutting unit. As to other configurations of the second embodiment, reference can be made to the descriptions thereon in the first embodiment, for example.

In the biological tissue cutting device of the present embodiment, it is preferable that, for example, with respect to a biological tissue fixed on the stage, the first cutting unit is disposed so as to cut a first direction of the biological tissue and the second cutting unit is disposed so as to cut a second direction and a third direction of the biological tissue. Specifically, in the device of the present embodiment, it is preferable that the cutting edges of the first cutting section in the first cutting unit and the second cutting section and the third cutting section in the second cutting unit extend in the first direction, the second direction, and the third direction with respect to the biological tissue, respectively.

Figure 8:
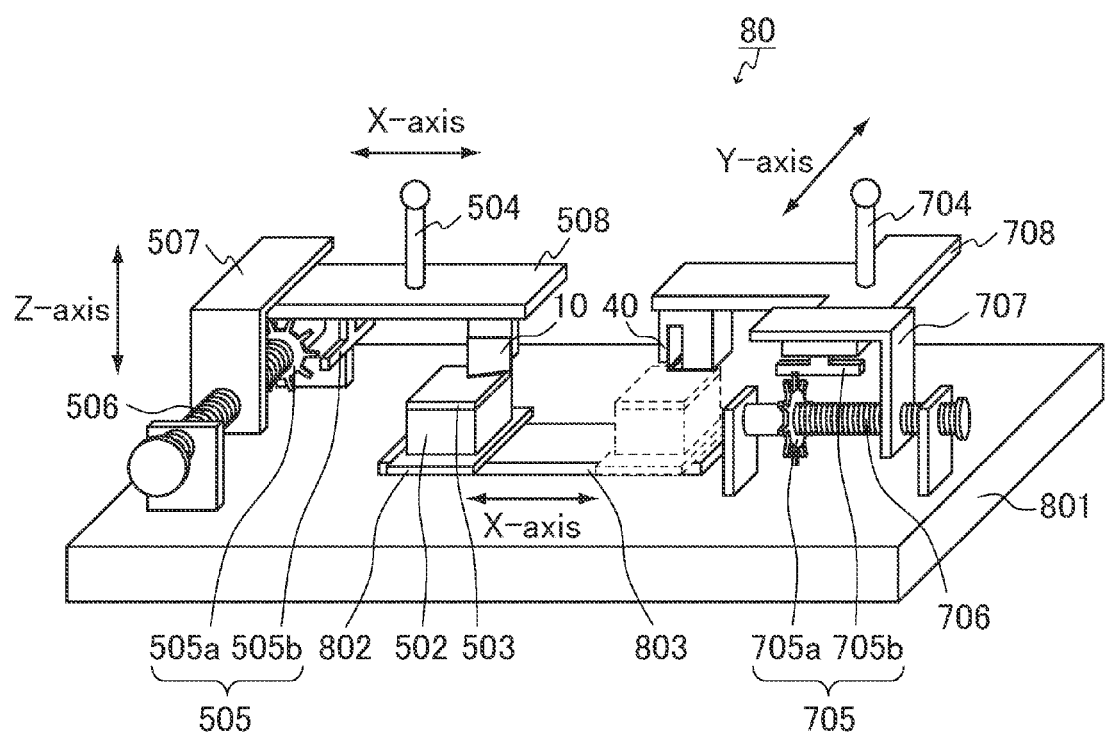
FIG. 8 is a perspective view schematically showing an integrated device provided with a first cutting unit and a second cutting unit in still another embodiment of the present invention.

FIG. 8 shows an example of a biological tissue cutting device of the present embodiment. FIG. 8 is a perspective view schematically showing the biological tissue cutting device of the present embodiment. In FIG. 8, the same components as those in FIGS. 6 and 7 are given the same reference numerals, and reference can be made to the descriptions thereon in the first embodiment, for example.

The biological tissue device of the present embodiment includes a stage unit, a first cutting unit, and a second cutting unit. These units are disposed on a substrate 801. With this configuration, they are included in a single component. In the present embodiment, descriptions regarding the directions are directed to a first direction, a second direction, and a third direction of a biological tissue fixed on the stage.

The stage unit includes: a stage on which a biological tissue is fixed; a mounting section on which the stage is mounted; and a stage movement control section that controls the movement of the stage. The stage is mounted to the mounting section. The mounting section can be moved in, for example, the first direction (X-axis direction), the second direction (Y-axis direction), and the third direction (Z-axis direction) by the stage movement control section. The stage movement control section is not particularly limited, and may be the combination of a rail (e.g., a linear guide) 803 and a slider 802. The mounting section can be moved in the first direction by disposing the mounting section on the slider and moving the slider along the rail. The stage in the stage unit preferably is fixed using, e.g., an engaging tool(s) such as a screw(s) or a plunger screw(s) in order to allow reliable positioning of the stage during the cutting of the biological tissue, for example.

The first cutting unit includes: a first cutting section; and a first movement control section that controls the movement of the first cutting section. The first cutting section is a blade of a cutter, for example, and the blade is disposed in such a manner that the cutting edge of the blade extends in the first direction. The first cutting section can be moved in the first direction (X-axis direction), the second direction (Y-axis direction), and the third direction (Z-axis direction) by the first movement control section. The movement in the first direction is, for example, movement between a cutting start position and a cutting end position. The movement in the second direction is, for example, movement in the second direction (Y-axis direction) for pulling the first cutting section out from the biological tissue and for setting a new cutting start position for the same layer in the height direction. The movement in the third direction is, for example, movement in the third direction (Z-axis direction) for setting a new cutting start position for a new layer in the height direction. The first movement control section is not particularly limited as long as it can control these movements. Regarding the first movement control section, reference can be made to the descriptions on the illustrative example of the first movement control section in the first embodiment, for example.

The second cutting unit includes: a second cutting section, a third cutting section, and a second movement control section that controls the movement of the second cutting section and the third cutting section. The second cutting section and the third cutting section each are a blade of a cutter, for example. The second cutting section is disposed in such a manner that the cutting edge of the blade extends in the second direction. The third cutting section is disposed in such a manner that the cutting edge of the blade extends in the third direction. The second cutting section and the third cutting section are fixed so that the blades maintain these directions. The second cutting section and the third cutting section can be moved in, for example, the first direction (X-axis direction), the second direction (Y-axis direction), and the third direction (Z-axis direction) by the second movement control section. The movement in the second direction is, for example, movement between a cutting start position and a cutting end position. The movement in the first direction is, for example, movement for setting a new cutting start position for the same layer in the height direction. The movement in the third direction is, for example, movement for setting a new cutting start position for a new layer in the height direction. The second movement control section is not particularly limited as long as it can control these movements. Regarding the second movement control section, reference can be made to the descriptions on the illustrative example of the second movement control section in the first embodiment, for example.

As to the integrated device of the present embodiment, the descriptions in the first embodiment also are applicable, except that the stage 503 on which a biological tissue is fixed is relocated from the first cutting unit to the second cutting unit. In the integrated device of the present embodiment, the biological tissue is cut by the first cutting section 10 of the first cutting unit, and thereafter, the stage unit (the stage mounting section 502 and the stage 503) on the slider 802 is moved toward the second cutting unit side along the rail so as to allow the biological tissue to be cut by the second cutting section 20 and the third cutting section 30 of the second cutting unit.

In the integrated device of the present embodiment, the stage unit may have a function of rotating in the planar direction, for example. With the rotating function of the stage unit, for example, even if the cutting direction of the blade of the first cutting section 10 in the first cutting unit and the cutting directions of the blades of the second cutting section 20 and the third cutting section 30 in the second cutting unit are not aligned in the X-axis direction and the Y-axis direction, it is possible to adjust the directions by rotating the stage unit at the time of cutting by the respective units.

(2) Biological Tissue Cutting Method

As described above, the method for cutting a biological tissue using the biological tissue cutting device according to the present invention includes: a fixing step of fixing a biological tissue on the stage; a first cutting step of cutting the biological tissue in a first direction by the first cutting unit; and a second cutting step of cutting the biological tissue in a second direction and a third direction simultaneously by the second cutting unit, wherein the second direction is a direction crossing the first direction, and the third direction is a direction crossing the first direction and the second direction.

The cutting method according to the present invention is characterized in that the biological tissue cutting device according to the present invention is used therein, and other configurations and conditions are not particularly limited. As to the cutting method of the present invention, reference can be made to the description regarding the biological tissue cutting device of the present invention.

The cutting method according to the present invention preferably is configured so that the first cutting step and the second cutting step are repeated. With this configuration, for example, a plurality of tissue fragments can be prepared easily from the biological tissue fixed on the biological tissue cutting device.

(3) Tissue Fragment Production Method

As described above, the tissue fragment production method according to the present invention is characterized in that the biological tissue is cut by the cutting method of the present invention.

The production method according to the present invention is characterized in that the biological tissue cutting device according to the present invention is used therein, and other configurations and conditions are not particularly limited. As to the production method of the present invention, reference can be made to the descriptions regarding the biological tissue cutting device of the present invention and the cutting method of the present invention.

(4) Regeneration Method, Surgical Operation Method, and Therapeutic Method

The method for regenerating a biological tissue according to the present invention is characterized in that a tissue fragment obtained by the production method according to the present invention is used therein, as described above.

The surgical operation method according to the present invention is characterized in that a tissue fragment obtained by the production method according to the present invention is used therein.

The therapeutic method according to the present invention is characterized in that a tissue fragment obtained by the production method according to the present invention is used therein.

These methods of the present invention are characterized in that a tissue fragment obtained using the biological tissue cutting device of the present invention is used therein, and other configurations and conditions are not particularly limited.

A subject to which these methods of the present invention are applicable is not particularly limited, and may be a human or a non-human animal. The regeneration method may be applied either in vitro or in vivo, for example.

While the present invention has been described above with reference to illustrative embodiments, the scope of the present invention is by no means limited or restricted by these illustrative embodiments. Various changes and modifications may be made without departing from the scope of the present invention.

This application claims priority from Japanese Patent Application No. 2014-014859 filed on Jan. 29, 2014. The entire disclosure of this Japanese patent application is incorporated herein by reference.

INDUSTRIAL APPLICABILITY

As specifically described above, the biological tissue cutting device of the present invention performs cutting in the first direction and simultaneous cutting in the second direction and the third direction, thereby allowing a large number of minute tissue fragments to be produced easily and accurately.

EXPLANATION OF REFERENCE NUMERALS

10: first cutting section
101, 201, 301, 401: main body
102, 202, 302: blade
20: second cutting section
30: third cutting section
40, 70: second cutting unit (Y and Z plane cutting unit)
50: first cutting unit (X plane cutting unit)
501, 701, 801: substrate
502, 702: stage mounting section
503: stage
504, 704: handle
505, 705: ratchet
505a, 705a: ratchet gear
505b, 705b: ratchet pawl
506, 706: feed screw
507, 707: feed nut
508, 708: mounting plate
60: biological tissue
80: integrated device
802: slider
803: rail

The invention claimed is:

1. A biological tissue cutting device for producing a tissue fragment by cutting a biological tissue, the biological tissue cutting device comprising:
a stage unit comprising a stage configured to fix the biological tissue;
a first cutting unit configured to form a cut surface extending in a first direction by cutting the biological tissue fixed on the stage; and
a second cutting unit configured to form a cut surface extending in a second direction and a cut surface extending in a third direction by cutting the biological tissue fixed on the stage, wherein
a planar direction of the cut surface extending in the second direction is a direction crossing the cut surface extending in the first direction,
a planar direction of the cut surface extending in the third direction is a direction crossing the cut surface extending in the first direction and the cut surface extending in the second direction,
the second cutting unit comprises:
a second cutting section that cuts the biological tissue to form the cut surface extending in the second direction;
a third cutting section that cuts the biological tissue to form the cut surface extending in the third direction; and
a second movement control section that moves the second cutting section and the third cutting section simultaneously,
the second cutting section and the third cutting section are integrated in such a manner that the cut surface extending in the second direction and the cut surface extending in the third direction formed by the second cutting section and the third cutting section maintain a fixed angle, and
the second movement control section simultaneously moves the second cutting section and the third cutting section from a cutting start position to a cutting end position of the biological tissue and then to a new cutting start position.

2. The biological tissue cutting device according to claim 1, wherein
the first cutting unit comprises:
a first cutting section that cuts the biological tissue to form the cut surface extending in the first direction; and
a first movement control section that moves the first cutting section, and
the first movement control section moves the first cutting section from a cutting start position to a cutting end position of the biological tissue and then to a new cutting start position.

3. The biological tissue cutting device according to claim 2, wherein
after the first movement control section has moved the first cutting section from the cutting start position to the cutting end position, the first movement control section moves the first cutting section away from the biological tissue and then to the new cutting start position.

4. The biological tissue cutting device according to claim 1, wherein
after the second movement control section has moved the second cutting section and the third cutting section from the cutting start position to the cutting end position of the biological tissue, the second movement control section moves the second cutting section and the third cutting section from the cutting end position to the cutting start position along the path, and further moves the second cutting section and the third cutting section to a new cutting start position.

5. The biological tissue cutting device according to claim 1, further comprising a stage movement control section, wherein
the stage movement control section moves the stage in at least one of an upper direction, a lower direction, and a planar direction relative to a surface of the stage on which the biological tissue is fixed.

6. The biological tissue cutting device according to claim 1, wherein
the first cutting unit and the second cutting unit are provided as separate components,
each of the first cutting unit and the second cutting unit comprises a stage mounting section,
the stage is mounted to the stage mounting section of the first cutting unit and the first cutting unit perform cutting of the biological tissue, and thereafter, the stage is detached from the first cutting unit and mounted to the second cutting unit and the second cutting unit performs cutting of the biological tissue.

7. The biological tissue cutting device according to claim 1, wherein
the first cutting unit and the second cutting unit are disposed in a single component, and
at least one of the stage, the first cutting unit, and the second cutting unit is detachable.

8. A method for cutting a biological tissue using the biological tissue cutting device according to claim 1, the method comprising:
a fixing step of fixing a biological tissue on the stage;
a first cutting step of cutting the biological tissue by the first cutting unit to form a cut surface extending in a first direction; and
a second cutting step of cutting the biological tissue by the second cutting unit to form a cut surface extending in a second direction and a cut surface extending in a third direction, wherein
a planar direction of the cut surface extending in the second direction is a direction crossing the cut surface extending in the first direction, and
a planar direction of the cut surface extending in the third direction is a direction crossing the cut surface extending in the first direction and the cut surface extending in the second direction.

9. The method according to claim 8, wherein
the biological tissue is at least one selected from the group consisting of cartilage, membrane tissues, skin tissues, vascular tissues, hormone-producing tissues, nerves, tendons, liver tissues, fat, and muscles.

10. The method according to claim 8, wherein
the biological tissue fixed on the stage is from 0.1 to 10 mm in thickness and from 50 to 10,000 $mm^2$ in area.

11. The method according to claim 8, wherein
the length of each side of a fragment of the biological tissue obtained through the cutting by the first cutting unit and the second cutting unit is in a range from 0.05 to 3 mm.

12. The method according to claim 8, wherein
the cut surface of the biological tissue in the first direction is substantially perpendicular to the surface of the stage, and the cut surface extending in the second direction of the biological tissue is substantially perpendicular to a surface of the stage,
the cut surface extending in the first direction is substantially perpendicular to the cut surface extending in the second direction, and
the cut surface of the biological tissue in the third direction is substantially parallel to the surface of the stage.

13. The method according to claim 8, wherein
the first cutting step and the second cutting step are repeated for the same biological tissue.

14. A method for producing a tissue fragment, the method comprising:
cutting a biological tissue by the method according to claim 8.

* * * * *